United States Patent
Watanabe et al.

(10) Patent No.: US 9,845,485 B2
(45) Date of Patent: Dec. 19, 2017

(54) **MICROALGAE OF THE GENUS *EUGLENA*, METHOD FOR PRODUCING POLYSACCHARIDES, AND METHOD FOR PRODUCING ORGANIC COMPOUND**

(71) Applicant: Kobelco Eco-Solutions Co., Ltd., Kobe-shi, Hyogo (JP)

(72) Inventors: Makoto Watanabe, Tsukuba (JP); Mikihide Demura, Tsukuba (JP); Masanobu Kawachi, Tsukuba (JP); Natsuki Sato, Hadano (JP); Akira Akashi, Kobe (JP); Jun Takezaki, Kobe (JP); Takeshi Hamada, Kobe (JP); Madoka Takahashi, Kobe (JP); Kenji Ohiraki, Kobe (JP)

(73) Assignee: Kobelco Eco-Solutions Co., Ltd., Kobe-shi (JP)

( * ) Notice: Subject to any disclaimer, the term of this patent is extended or adjusted under 35 U.S.C. 154(b) by 32 days.

(21) Appl. No.: 14/779,168

(22) PCT Filed: Mar. 24, 2014

(86) PCT No.: PCT/JP2014/058063
§ 371 (c)(1),
(2) Date: Sep. 22, 2015

(87) PCT Pub. No.: WO2014/157077
PCT Pub. Date: Oct. 2, 2014

(65) Prior Publication Data
US 2016/0122789 A1   May 5, 2016

(30) Foreign Application Priority Data

Mar. 27, 2013  (JP) ................. 2013-067558

(51) Int. Cl.
| | |
|---|---|
| C12P 19/04 | (2006.01) |
| C12N 1/12 | (2006.01) |
| C12R 1/89 | (2006.01) |
| C12P 1/00 | (2006.01) |
| C12P 7/64 | (2006.01) |

(52) U.S. Cl.
CPC ............. *C12P 19/04* (2013.01); *C12N 1/12* (2013.01); *C12P 1/00* (2013.01); *C12P 7/64* (2013.01); *C12P 7/6436* (2013.01); *C12R 1/89* (2013.01)

(58) Field of Classification Search
None
See application file for complete search history.

(56) References Cited

FOREIGN PATENT DOCUMENTS

| | | |
|---|---|---|
| JP | 59118090 A | 7/1984 |
| JP | 6113819 A | 4/1994 |
| JP | 770207 A | 3/1995 |

OTHER PUBLICATIONS

Hwang et al. "Euglena anabaena 18S ribosomal RNA gene, complete sequence; mitochondrial gene for mitochondrial product", 1998.
Kawachi et al., "MCC-NIES List of Strains: Microalgae, Endangered Macroalgae and Protists", 9th Edition, 2013, http://mcc.nies.go.jp/.
Sheveleva et al., "Identification and comparative analysis of the chloroplast alpha-subunit gene of DNA-dependent RNA polymerase from seven *Euglena* species", Nucleic Acids Research, 2002, pp. 1247-1254, vol. 30:5.
Shin et al. "Ultrastructure of *Euglena anabaena* var. *minor*", Phycological Research, 2000, pp. 19-25, vol. 48.
Barsanti et al., "Paramylon (β-1,3-glucan) content in wild type and WZSL mutant of Euglena gracilis. Effects of growth conditions", Journal of Applied Phycology, 2001, vol. 13, pp. 59-65, Kluwer Academic Publishers, Netherlands.
Rodriguez-Zavala et al., "Increased synthesis of α-tocopherol, paramylon and tyrosine by Euglena gracilis under conditions of high biomass production", Journal of Applied Microbiology, 2010, vol. 109:6, pp. 2160-2172, The Society for Applied Microbiology.
Santek et al., "Production of paramylon, a β-1,3-glucan, by heterotrophic cultivation of Euglena gracilis on a synthetic medium", Engineering Life Sciences, 2009, vol. 9:1, pp. 23-28, Wiley InterScience.
"Euglena gracilis partial 18S rRNA gene, strain SAG 1224-5/25," European Nucleotide Archive, Apr. 1, 2003, Sequence AJ532426, European Molecular Biology Laboratory.
"Euglena UTEX364 small subunit ribosomal RNA gene, complete sequence," European Nucleotide Archive, Jun. 21, 1999, Sequence AF112873, European Molecular Biology Laboratory.
Santek et al.; "Production of paramylon, a B-1,3-glucan, by heterotrophic cultivation of Euglena gracilis on potato liquor"; Eng. Life Sci.; 2010; pp. 165-170; vol. 10:2.

*Primary Examiner* — Vera Afremova
(74) *Attorney, Agent, or Firm* — The Webb Law Firm

(57) ABSTRACT

Provided are microalgae of the genus *Euglena* that fall under *Euglena gracilis* strain EOD-1 (Accession No. FERM BP-11530) or its mutant strain and that are capable of producing at least polysaccharides. Further provided is a method for producing polysaccharides including: culturing microalgae of the genus *Euglena* that fall under *Euglena gracilis* strain EOD-1 (Accession No. FERM BP-11530) or its mutant strain and that are capable of producing at least polysaccharides as polysaccharide-producing organisms to produce the polysaccharides. Further provided is a method for producing an organic compound including: culturing microalgae of the genus *Euglena* that fall under *Euglena gracilis* strain EOD-1 (Accession No. FERM BP-11530) or its mutant strain and that are capable of producing at least polysaccharides to produce at least one organic compound selected from the group consisting of polysaccharides, lipids, vitamin C, vitamin E, pigments, and proteins.

6 Claims, 6 Drawing Sheets

| Sequence No.(1960 in total) | 93 | 94 | 108 | 156 | 221 | 251 | 396 | 742 | 785 | 852 | 1000 | 1334 | 1439 | 1440 | 1460 | 1636 | 1785 | 1779 |
|---|---|---|---|---|---|---|---|---|---|---|---|---|---|---|---|---|---|---|
| EOD-1 | G | C | T | A | T | T | - | T | T | C | G | G | C | A | C | G | C | A |
| NIES-47 | T | G | C | G | A | C | - | C | T | T | G | T | C | A | C | A | T | C |
| NIES-48(Z) | G | C | C | G | A | C | - | C | C | C | G | T | C | A | C | A | T | A |
| NIES-48(Z, M12677) | G | C | C | G | A | C | - | C | C | C | - | T | C | A | C | A | T | A |
| NIES-49 | G | C | C | G | A | C | - | C | T | T | G | T | C | A | C | A | T | A |
| SAG1224-5/15 | G | C | C | G | A | C | - | C | T | T | G | T | G | C | G | A | T | A |
| SAG1224-5/25 | G | C | C | G | A | C | - | C | C | C | G | T | C | A | C | A | T | A |
| AY029409 | G | C | C | G | A | C | A | C | T | T | G | T | C | A | C | A | T | A |

SEQUENCE LISTING

```
<160> NUMBER OF SEQ ID NOS: 4

<210> SEQ ID NO 1
<211> LENGTH: 1960
<212> TYPE: DNA
<213> ORGANISM: Euglena gracilis

<400> SEQUENCE: 1
gtgtgctcgg tccacctgca aggacccat  tggacatcca  ccaaaacctt  gtggctaata      60
cacgttcgac ccagtcagcc atgcaacact cggcagggat cctgtcttcg gacagtccct     120
tcaccggtgg tggcggatgt atgcccagct gatacaaaga ccagcggccg caaggccagt     180
gtgttggcat ggttgactca ggctggccct ccgtggccgc tgtgctggtg gatttcgtgc     240
atgcctcgtg tatgccccac ttgatcgcaa gagcttctga cctatcagct tgactgtggt     300
gtatcggacc acagtggcct tgacgggtaa cggagaatca gggttcgatt ccggagaggg     360
agcctgagag acggctacca ctaccaaggt gggcagcagg cacgcaaatt gccccatgca     420
aagacagtct gtgaggcagc gacgaacagt agcaaccccg tcggccttac gtgccgatgg     480
ggcttggaat ggacgctatc caaagacagc cgtgagtatc aaccggaggg caagtctggt     540
gccagcagct gcggtaattc cagctccgag ggcgtatact aacattgctg ctgttaaaac     600
acttgtagtc tgcctacggg ctgcaggtct gctgggtggc cggtttgttg tttctctggc     660
cagggaagga cctcggttcg accctgtgtt gggctgcaac ggctggactc aaccccagt      720 ggtacgtccc tgcgcccacc tttcagtcga tggtgagatc tgctcctgcc aaaagtctgc     780
ttcattgcag gccaaagcgg tttatgcctc ccgcactggc aacggacacc aacaggggac     840
ccagcctcga gctgggtagt ctacctctgg tccaccaccg gagcccaccg tcttcgacac     900
cctggaaaac tcagtgtgct caaagcatcc ccgcgacggc tgaatgtcca tccatggaat     960
gtcaaggcat cgaccaagtg tggcattgga gttgtgctgg ccttggggcc cactctggac    1020
aacctggtgg tgtgttcctg caggatcaac aggatcgttg ccctgcctgg ccttcgggtc    1080
tcgtcaggct tcgtcccctg tccctgcagc ttgcacccat cgatcgtaag tgatgggact    1140
gttcggggtg aaagatacgg gagcgccaga ggtgaaattc ttagatcgct gccagatcca    1200
ctgcagcgaa ggcgttctgc aagtgcacgt ccgtcgatca agaatgagag ttcggggagc    1260
aaagatgatc agacaccgtc gtagtccggc cactgtaaac gatgccggcc aggccttggc    1320
```

```
agagcaagaa tccgagactc tgtcagggcc actcctccca caacgagaaa tccacagcct    1380
gtgggttcag gggggagtac tgtcgcaagg ctgaaactta aaggaattga cggaatggca    1440
ccacaaggcg tggagtatgc ggcttaattt gactcaacgc ggggaatgtt accaggtcag    1500
gacgcaactg ggattgacag attgagagct ctttcttgat cttgtggacg gtggtgcatg    1560
gccgctcctg attggtggag tgatttgtct ggttgattcc gataacgagt gagacatctg    1620
cctcccacta gcctggggct cgcatttggt agggttcggc tgctcggtgg cagcccctg     1680 gcaacagggg gagatgtacc ggtgcatgct cccgagagcc tccagttcag cttctctgag    1740
gtgctgtgtc cgccacaaag ggcacgcatg ctagagccaa cagcaggtct gtgatgctcc    1800
cagatgtcct gggccgcacg cgcactacat tgtcacagtg aaggtgtcga catgcccact    1860
ccggtgggcc ctggcctgaa gaggctggga aatcctgcaa gcctgtgacg tactggggat    1920
agatggttgc aactgtctgc cttgaacgtg gaatgcctag                          1960

<210> SEQ ID NO 2
<211> LENGTH: 11
<212> TYPE: DNA
<213> ORGANISM: Artificial Sequence
<220> FEATURE:
<223> OTHER INFORMATION: Primer 1

<400> SEQUENCE: 2
aaatcgggct g                                                         11

<210> SEQ ID NO 3
<211> LENGTH: 10
<212> TYPE: DNA
<213> ORGANISM: Artificial Sequence
<220> FEATURE:
<223> OTHER INFORMATION: Primer 2

<400> SEQUENCE: 3
atcgggtccg                                                           10

<210> SEQ ID NO 4
<211> LENGTH: 10
<212> TYPE: DNA
<213> ORGANISM: Artificial Sequence
<220> FEATURE:
<223> OTHER INFORMATION: Primer 3

<400> SEQUENCE: 4
gcgatcccca                                                           10
```

MICROALGAE OF THE GENUS *EUGLENA*, METHOD FOR PRODUCING POLYSACCHARIDES, AND METHOD FOR PRODUCING ORGANIC COMPOUND

CROSS-REFERENCE TO RELATED APPLICATION

This application is the United States national phase of International Application No. PCT/JP2014/058063 filed Mar. 24, 2014, and claims priority to Japanese Patent Application No. 2013-067558 filed Mar. 27, 2013, the disclosures of which are hereby incorporated in their entirety by reference.

The Sequence Listing associated with this application is filed in electronic format via EFS-Web and is hereby incorporated by reference into the specification in its entirety. The name of the text file containing the Sequence Listing is 159687_ST25.txt. The size of the text file is 3,595 bytes, and the text file was created on Sep. 17, 2015.

FIELD

The present invention relates to microalgae of the genus *Euglena*, a method for producing polysaccharides, and a method for producing an organic compound.

BACKGROUND

Microalgae of the genus *Euglena* are also called *Euglena*, and are known as microorganisms that produce polysaccharides such as paramylum or the like by being cultured.

Various microalgae of the genus *Euglena* are conventionally known. For example, *Euglena gracilis* strain NIES-48 is known (Patent Literature 1).

Such microalgae of the genus *Euglena* produce polysaccharides such as paramylum by being cultured, and store the polysaccharides in their cells.

Further, the microalgae of the genus *Euglena* can convert the stored polysaccharides into wax esters or can further produce proteins while producing the polysaccharides, depending on the culture conditions. Then, the organic compounds such as polysaccharides, lipids, and proteins that are produced and stored in the cells of the microalgae can be used in applications such as fuel and food.

However, the microalgae of the genus *Euglena* have a problem that the performance to produce an organic compound such as polysaccharides is not necessarily sufficient.

CITATION LIST

Patent Literature

Patent Literature 1: JP H07-070207 A

SUMMARY

Technical Problem

In view of the above and other problems, it is an object of the present invention to provide microalgae of the genus *Euglena* that are capable of sufficiently producing at least polysaccharides. It is another object of the present invention to provide a method for producing polysaccharides that allows the polysaccharides to be sufficiently obtained. It is still another object of the present invention to provide a method for producing an organic compound that allows at least one organic compound selected from the group consisting of polysaccharides, lipids, vitamin C, vitamin E, pigments, and proteins to be sufficiently obtained.

Solution to Problem

In order to solve the aforementioned problem, microalgae of the genus *Euglena* according to the present invention are characterized by being *Euglena gracilis* strain EOD-1 (Accession No. FERM BP-11530) or its mutant strain and being capable of producing at least polysaccharides.

A method for producing polysaccharides according to the present invention is characterized by culturing microalgae of the genus *Euglena* that fall under *Euglena gracilis* strain EOD-1 (Accession No. FERM BP-11530) or its mutant strain and that are capable of producing at least polysaccharides as polysaccharide-producing organisms to produce the polysaccharides.

According to one aspect of the method for producing polysaccharides of the present invention, a broth used in the culture may contain 15 to 30 g/L of glucose.

According to another aspect of the method for producing polysaccharides of the present invention, the broth used in the culture may contain yeast lysate.

According to still another aspect of the method for producing polysaccharides of the present invention, the broth used in the culture may have a composition of AF6 culture medium.

According to still another aspect of the method for producing polysaccharides of the present invention, the polysaccharides may be paramylum.

A method for producing an organic compound according to the present invention is characterized by culturing microalgae of the genus *Euglena* that fall under *Euglena gracilis* strain EOD-1 (Accession No. FERM BP-11530) or its mutant strain and that are capable of producing at least polysaccharides to produce at least one organic compound selected from the group consisting of polysaccharides, lipids, vitamin C, vitamin E, pigments, and proteins.

DETAILED DESCRIPTION OF EMBODIMENTS

Figures 1, 2:
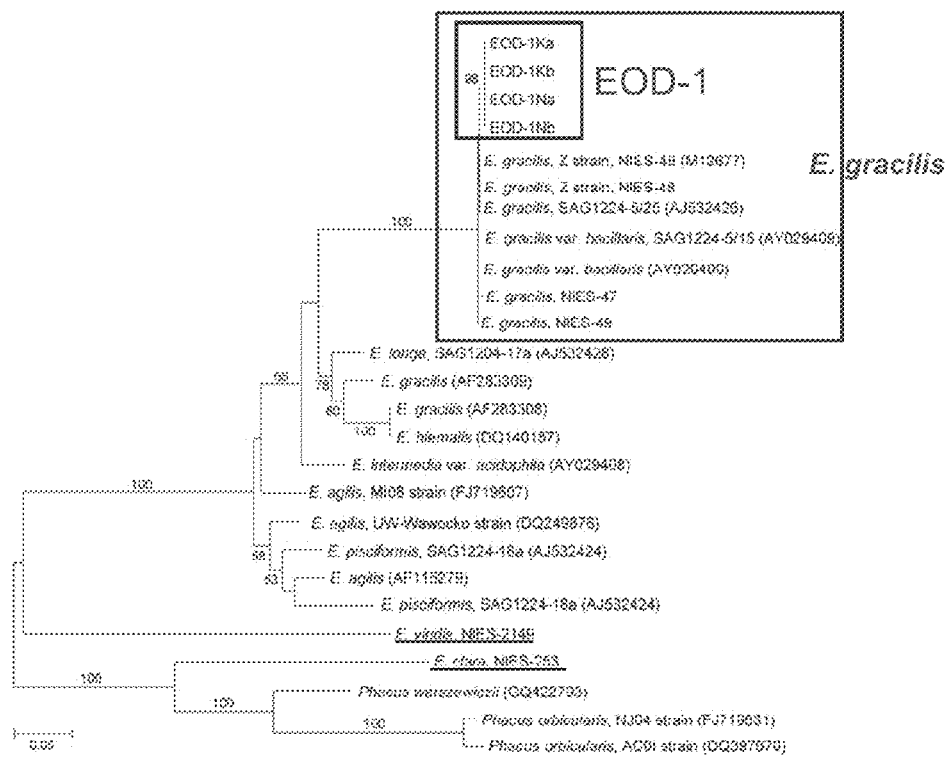
FIG. 1 is a comparison table for base sequence of the 18S rRNA gene of *Euglena gracilis*.
FIG. 2 is a phylogenetic tree constructed using the 18S rRNA gene.

Hereinafter, an embodiment of microalgae of the genus *Euglena* according to the present invention is described in detail.

The microalgae of the genus *Euglena* according to this embodiment (hereinafter, simply referred to as microalgae of the genus *Euglena* or microalgae) are *Euglena gracilis* strain EOD-1 (Accession No. FERM BP-11530) or its mutant strain and that are capable of producing at least polysaccharides.

The microalgae of the genus *Euglena* of this embodiment has an effect of enabling at least polysaccharides to be sufficiently produced.

The microalgae of the genus *Euglena* are organisms that inhabit while floating in water. Further, the microalgae of the genus *Euglena* are unicellular micro algae with a size of about 10 µm to 50 µm, which differs depending on strains.

The properties of the microalgae of the genus *Euglena* are described in detail below.

Morphological Properties of Microalgae of the Genus *Euglena*

The vegetative cells of the microalgae of the genus *Euglena* have flagellum and actively move. Further, each cell has an almost fusiform shape. The cell includes a red organelle called eyespot in addition to general organelles such as the nucleus, chloroplasts, and mitochondria.

Physiological or Biochemical Properties of Microalgae of the Genus *Euglena*

(1) Culture medium: A broth mainly composed of freshwater can be used for growth (organic matter derived from wastewater also can be used for growth).

(2) Photosynthetic ability: Photoautotrophic growth by photosynthesis is possible.

(3) Contained pigments: Chlorophyll a, chlorophyll b, and other carotenoids are contained.

(4) Anabolic storage substances: Proteins, lipids (wax esters), and polysaccharides (paramylum)

(5) Growth temperature range: 15° C. to 35° C. (optimum temperature: 25° C.)

(6) pH range suitable for growth: pH 3.5 to 5.5 (however, growth is possible at a pH outside the aforementioned range)

Genetic Information of Microalgae of the Genus *Euglena*.

The microalgae of the genus *Euglena* have the 18S rDNA (18S rRNA gene) represented by SEQ ID No: 1

The 18S rRNA gene can be analyzed by a method commonly used as a method for identifying microalgae. Specifically, the 18S rRNA gene can be analyzed, for example, by a method described in EXAMPLES.

The base sequence of the 18S rRNA gene of the microalgae of the genus *Euglena* can be compared with the base sequence of the 18S rRNA gene of known microalgae of the genus *Euglena* obtained from GenBank using the BLAST homology search. The results of the comparison with the known microalgae of the genus *Euglena* on the sequence homology matching degree will be shown in EXAMPLES below.

As the database, EMBL and DDBJ can be also used, for example.

Further, a molecular phylogenetic tree can be constructed using a molecular phylogenetic tree drawing software Mega 5 program (Tamura et al., 2011, Mol. Biol. Evol. 28: 2731-2739) by the maximum-likelihood method. The constructed molecular phylogenetic tree will be shown in detail in EXAMPLES below.

Using the technique as described above, the aforementioned microalgae of the genus *Euglena* were identified from the later-described results in EXAMPLES as *Euglena gracilis* and named *Euglena gracilis* strain EOD-1.

The *Euglena gracilis* strain EOD-1 has been internationally deposited in Patent Organism Depositary, National Institute of Technology and Evaluation (NITE-IPOD: 2-5-8-120 Kazusakamatari, Kisarazu, Chiba 292-0818 Japan) on Jun. 28, 2013 (Original date of deposit: Mar. 25, 2013) as Accession No. FERM BP-11530 under the provisions of the Budapest Treaty.

As has been described above, the microalgae of the genus *Euglena* have chloroplasts in their cells, and therefore can grow by photosynthesis. That is, the microalgae of the genus *Euglena* are photoautotrophs.

Further, the microalgae of the genus *Euglena* can grow also by using organic nutrients such as glucose as their nutrients. That is, the microalgae of the genus *Euglena* are also heterotrophs.

In this way, the microalgae of the genus *Euglena* can grow only by photoautotrophy, can grow only by heterotrophy, or can grow by concurrent photoautotrophy and heterotrophy.

The mutant strain is produced, for example, by applying a common mutation process, adaptation by subculture, or natural mutation.

The mutation process can be performed using common mutagens. Examples of the mutagens include drugs having mutagenic activity and ultraviolet rays. Examples of the drugs having mutagenic activity include nucleotide base analogs such as streptomycin, ofloxacin, ethyl methane sulfonate, and N-methyl-N'-nitro-N-nitrosoguanidine, and bromouracil, and acridines.

Next, an embodiment of the method for producing polysaccharides according to the present invention is described.

According to the method for producing polysaccharides of this embodiment, at least polysaccharides are produced by culturing the microalgae of the genus *Euglena*.

The method for producing polysaccharides of this embodiment has an effect of enabling polysaccharides to be sufficiently obtained.

Specifically, the method for producing polysaccharides of this embodiment includes a culture step of culturing the microalgae of the genus *Euglena* in a broth containing at least water.

The broth preferably contains water and nutrients that promote the growth of the microalgae.

Examples of the nutrients include inorganic nutrients and organic nutrients.

Examples of the inorganic nutrients include nitrogen-containing inorganic compounds and phosphorus-containing inorganic compounds. Further, examples of the inorganic nutrients include potassium ion, iron ion, manganese ion, cobalt ion, zinc ion, copper ion, molybdenum ion, and nickel ion.

The concentration of the inorganic nutrients in the broth is generally about a concentration that is commonly known.

Examples of the organic nutrients include monosaccharides such as glucose and fructose, vitamins such as vitamins $B_6$ and $B_{12}$, amino acids such as arginine, aspartic acid, glutamic acid, glycine, and histidine, organic acids such as malic acid, citric acid, succinic acid, and acetic acid, and alcohols such as ethanol.

Examples of the composition of the broth to be employed include the composition of "AF-6 culture medium", the composition of "Cramer-Myers culture medium", the composition of "Hutner culture medium", which will be described below, or a composition similar to these compositions.

In the culture step, the broth preferably contains 15 to 30 g/L of glucose as a carbon source. Further, the broth preferably contains yeast lysate (which will be described below). Further, the broth preferably has the composition of the AF6 culture medium.

The culture step can be carried out, for example, in a bath containing a mixture of the aforementioned broth and the microalgae.

In the culture step, photosynthesis of the microalgae can be caused by irradiating the microalgae with light. That is, in the culture step, photoautotrophic culture can be performed.

When the microalgae are irradiated with light in the culture step, the microalgae introduce carbon dioxide into their cells by photosynthesis, and can grow while producing at least polysaccharides such as paramylum. Further, the microalgae can grow while producing proteins and secondary metabolites such as lipids, pigments, and vitamins.

The light with which the microalgae are irradiated in the culture step is not specifically limited as long as it causes photosynthesis of the microalgae. As the light, natural light from the sun or artificial light such as illumination is, for example, employed.

The intensity of the light irradiation in the photoautotrophic culture step is not specifically limited, but is generally 50 $\mu mol/m^2 \cdot s$ to 200 $\mu mol/m^2 \cdot s$.

In the culture step, a period during which the microalgae are irradiated with light and a period during which the microalgae are not irradiated with light can be alternately repeated.

That is, a period during which photoautotrophic culture is performed and a period during which photoautotrophic culture is not performed can be alternately repeated in the culture step.

The period of the light irradiation in the culture step is generally 8 hours to 15 hours, which is equivalent to daytime during which sunlight shines. Further, the period of dark conditions during which the light irradiation is not performed for inhibiting the photosynthesis of the microalgae is generally 9 hours to 16 hours, which is equivalent to night-time during which sunlight does not shine. These periods can be changed depending on the situation or the purpose.

The dark conditions in which the light irradiation is not performed are the conditions in which the photosynthetic photon flux density (PPFD) is 50 $\mu mol/m^2 \cdot s$ or less.

Meanwhile, heterotrophic culture in which the microalgae are cultured in the presence of the organic nutrients included in the aforementioned nutrients can be carried out in the culture step. When the microalgae are cultured in the presence of the organic nutrients in the culture step, the microalgae introduce the organic nutrients into their cells, and can grow while producing at least polysaccharides such as paramylum.

That is, at least one of photoautotrophic culture and heterotrophic culture can be performed in the culture step.

It is preferable that both of the photoautotrophic culture and heterotrophic culture be performed in the culture step at the same time, in that the growth of the microalgae can be further promoted. That is, it is preferable that photoheterotrophic culture be performed in the culture step.

It is preferable to employ, as the organic nutrients used in the heterotrophic culture and photoheterotrophic culture, alcohols such as ethanol, monosaccharides such as glucose and fructose, or wastes containing these components that can be used by the microalgae of the genus *Euglena*, for example. Further, it is preferable that yeast or yeast lysate (hereinafter, referred to also as yeast extract) be used in combination as the organic nutrients, in that the growth of the microalgae of the genus *Euglena* can be more reliably promoted.

Examples of materials containing at least a part of the aforementioned organic nutrients include brewed beverages, distilled beverages, sake lees, shochu lees, molasses, and blackstrap molasses. Such alcoholic beverages can be used as a supply source of the organic nutrients in the heterotrophic culture and photoheterotrophic culture.

The brewed beverages are produced by alcoholic fermentation of a raw material containing sugar content with yeast, and are not distilled.

The brewed beverages are not distilled, and contain metabolites of alcoholic fermentation with yeast. Therefore, they contain nutrients including saccharides such as glucose produced by yeast, proteins, amino acids, vitamins, phosphorus, and potassium, other than ethanol and water.

Examples of the brewed beverages include beer, sake, wine, a brewed beverage using grains as a raw material, a brewed beverage using legumes as a raw material, a brewed beverage using potatoes as a raw material, and a brewed beverage using sugar as a raw material.

The beer is produced by saccharification of starch contained in at least malt with enzyme contained in the malt, thereby producing sugar, followed by alcoholic fermentation of the sugar with beer yeast. That is, the beer in this description includes products further using other raw materials, as long as they are produced as described above using at least malt as a raw material.

As the malt, barley malt is generally used.

The sake (Japanese sake) is produced by saccharification of starch contained in rice with rice malt, thereby producing sugar, followed by alcoholic fermentation of the sugar with yeast.

The wine is produced by alcoholic fermentation of at least grape juice with yeast.

Examples of the yeast include organisms belonging to the genus *Saccharomyces*, specifically, *Saccaromyces cerevisiae*.

Further, examples of the yeast include so-called sake yeast, so-called wine yeast, and so-called beer yeast.

Examples of the yeast lysate (yeast extract) include yeast autolysate generated by autolysis of the yeast, yeast whose cell walls are broken by contact with hot water, and yeast whose cell walls are broken by enzyme.

In the culture step, a gas containing oxygen can be supplied to the broth in order to maintain oxygen breathing of the microalgae. Further, in the culture step, a gas containing carbon dioxide can be supplied to the broth in order to promote the photosynthesis of the microalgae.

Such gases can be supplied by aerating the broth or stirring the broth, for example.

Specifically, in the culture step, the broth can be aerated, for example, with air in order to supply oxygen for breathing to the microalgae. Further, in the culture step, the broth can be aerated, for example, with an exhaust gas containing a comparatively large amount of carbon dioxide in order to promote the photosynthesis of the microalgae.

In the culture step, it is preferable that photoautotrophic culture and heterotrophic culture be performed at the same time, while oxygen and carbon dioxide are supplied into the broth, for example, by aeration. That is, in the culture step, it is preferable that photoheterotrophic culture be performed by irradiation with light and heterotrophic culture be performed in the presence of organic nutrients, concurrently, while a gas containing both of oxygen and carbon dioxide is supplied to the broth by aeration or the like in order to promote the oxygen breathing and photosynthesis of the microalgae.

In the culture step, the photosynthesis of the microalgae can be promoted by supplying carbon dioxide to the broth, while the microalgae are irradiated with light, for example, during daytime. Further, the heterotrophic culture of the microalgae can be performed by supplying air to the broth in the presence of organic nutrients, for example, during night-time when the microalgae are not irradiated with light.

Performing the culture step in this way is advantageous in that the growth of the microalgae is further promoted, and the production of paramylum or the like by the microalgae is further promoted.

The culture temperature in the culture step is not specifically limited as long as the microalgae can grow at the temperature. Specifically, a culture temperature (temperature of the broth), for example, of 15° C. to 35° C., preferably 20° C. to 30° C., is employed.

The pH of the broth in the culture step is not specifically limited as long as the microalgae can grow at the pH. A pH, for example, of 2.5 to 5.5 is employed.

For adjusting the pH of the broth, an inorganic acid such as hydrochloric acid may be added to the broth, or an organic acid such as acetic acid may be added to the broth. Adding an organic acid to the broth is advantageous in that the microalgae can grow using the organic acid as an organic nutrient.

Further, for adjusting the pH of the broth, an alkaline agent may be added to the broth. As the alkaline agent, sodium hydroxide, potassium hydroxide, or the like is generally used.

In the culture step, the oxygen supply to the broth can be suppressed for allowing the microalgae of the genus *Euglena* to produce wax esters.

Specifically, the microalgae can be cultured under anaerobic conditions in the culture step, for example, by stopping the aeration of the broth or supply an oxygen-free inert gas or the like to the broth.

In the culture step, the microalgae that have stored polysaccharides such as paramylum in their cells are further cultured under anaerobic conditions, thereby allowing the microalgae of the genus *Euglena* to convert the paramylum into wax esters so as to store the lipids in their cells.

In the culture step, it is preferable that the microalgae be cultured under anaerobic conditions and dark conditions without light irradiation, in that the production of wax esters can be further promoted.

Meanwhile, in the culture step, the microalgae can be cultured in the presence of inorganic nutrients containing nitrogen or organic nutrients containing nitrogen, while oxygen is supplied to the broth, in order to allow the microalgae of the genus *Euglena* to produce proteins.

In the culture step, the microalgae are cultured as described above, thereby allowing the microalgae to produce organic compounds such as polysaccharides, lipids, or proteins while the microalgae grow. Thus, such organic compounds can be stored in the cells of the microalgae.

Further, in the culture step, the culture conditions are appropriately adjusted, thereby allowing the microalgae to produce organic compounds such as pigments, vitamins such as vitamin C and vitamin E, proteins, and fatty acids including saturated fatty acids, advanced unsaturated fatty acids such as linolenic acid, arachidonic acid, and eicosapentaenoic acid, other than the aforementioned organic compounds.

Then, the microalgae storing these organic compounds in their cells can be used as biomass available for various applications such as food, pharmaceutical, feed, chemical products, and fuel.

Examples of the polysaccharides include paramylum ($\beta$-1,3-glucan). The paramylum is formed by bonding of about 700 units of glucose.

Examples of the lipids include wax esters. The wax esters are formed by ester bonding between higher fatty acids and higher alcohols. As the wax esters, wax esters formed by ester bonding between C-14 fatty acid and C-14 higher alcohol can be mentioned.

In the method for producing polysaccharides of this embodiment, the same steps as in the method for producing an organic compound, which will be described below, can be carried out.

Subsequently, an embodiment of the method for producing an organic compound according to the present invention is described.

According to the method for producing an organic compound of this embodiment, at least one selected from the group consisting of polysaccharides, lipids, vitamin C, vitamin E, pigments, and proteins is produced as the organic compound by carrying out the aforementioned culture method (culture step).

The method for producing an organic compound of this embodiment has an effect of enabling at least one organic compound selected from the group consisting of polysaccharides, lipids, vitamin C, vitamin E, pigments, and proteins to be sufficiently obtained.

Among these, vitamin C, vitamin E, pigments, and proteins can be produced together with polysaccharides by carrying out the method for producing polysaccharides.

Preferably, the method for producing an organic compound of this embodiment includes the aforementioned culture step, and further includes a thickening step of increasing the ratio of the microalgae after being cultured and a drying step of drying the microalgae by further reducing the moisture in the microalgae after the thickening step. In the method for producing an organic compound, the thickening step and the drying step are not necessarily needed.

The thickening step can be performed, for example, by using a common thickener.

Specifically, examples of the thickener include a device that concentrates the microalgae by increasing the ratio of the microalgae, for example, using floatation thickening, gravity thickening, thickening using membrane filtration, or belt thickening. Further, a dehydrator can be used as the thickener in order to further increase the ratio of the microalgae.

Specifically, examples of the dehydrator include a vacuum dehydrator, a pressure dehydrator (filter press), a belt press, a screw press, a centrifugal dehydrator (screw decanter), and a multi-disk dehydrator.

The thickening step may be performed using only the thickener, or may be performed using both of the thickener and the dehydrator, depending on applications of polysaccharides, lipids, proteins, or the like to be produced.

The drying step can be performed, for example, by heating the microalgae after the thickening step or placing the microalgae after the thickening step under reduced pressure.

Since the microalgae after the thickening step or the microalgae after the drying step can contain at least one of polysaccharides, lipids, vitamin C, vitamin E, pigments, and proteins in their cells, they can be used as they are in applications such as food.

Further, at least one of polysaccharides, lipids, vitamin C, vitamin E, pigments, and proteins is extracted from the microalgae as an organic compound by subjecting the microalgae after the thickening step or the microalgae after the drying step to a common extraction process, as needed. The extracted organic compound can be used in applications such as food raw materials and fuel.

Examples of the extraction process to be employed include an extraction process of extracting the aforementioned organic compound using an organic solvent such as ethanol and hexane, and an extraction process of extracting the aforementioned lipids or the like using a $CO_2$ solvent in an subcritical state.

The microalgae of the genus *Euglena*, the method for producing polysaccharides, and the method for producing an organic compound according to the aforementioned embodiments are as exemplified above. However, the present invention is not limited to the microalgae of the genus *Euglena*, the method for producing polysaccharides, and the method for producing an organic compound exemplified above.

Further, it is also possible to employ various embodiments that are commonly used in microalgae of the genus *Euglena*, a method for producing polysaccharides, and a method for producing an organic compound, as long as the effects of the present invention are not impaired.

That is, the present invention is not limited to the above described embodiments, and the design can be appropriately modified within the scope intended by the present invention. The operational advantage of the present invention is also not limited to the foregoing embodiments.

The embodiments disclosed herein should be construed in all respects as illustrative but not limiting. The scope of the present invention is not indicated by the foregoing description but by the scope of the claims. Further, the scope of the present invention is intended to include all the modifications equivalent in the sense and the scope to the scope of the claims.

EXAMPLES

Next, the present invention is described further in detail by way of examples. However, the present invention is not limited to these examples.

Collection and Isolation of Microalgae of the Genus *Euglena*

Lake water collected in lakes and marshes in Nagasaki was inoculated into AF-6 culture medium (which will be described below), which was cultured for two months at room temperature while being irradiated with fluorescent light.

Target microalgae in the culture medium after the culture were isolated with a micro pipette. The isolated microalgae were cultured in the AF-6 culture medium at room temperature while being irradiated with fluorescent light.

Identification of Microalgae of the Genus *Euglena*

Determination of Base Sequence

For confirming that the isolated microalgae were the species belonging to the genus *Euglena*, the following operations were performed.

That is, the base sequence of the 18S rRNA gene of the cultured microalgae of the genus *Euglena* was determined by a DNA sequencer ("CEQ8000", manufactured by Beckman Coulter, Inc.) using a primer set dedicated to the 18S rRNA gene of the microalgae of the genus *Euglena* (Zakrys et al., 2002, Journal of Phycology 38: 1190-1199). The determined base sequence is shown as Sequence No. 1 in the sequence listing.

Comparison of Base Sequence

The determined base sequence was compared with the base sequence of the 18S rRNA gene of known microalgae of the genus *Euglena* obtained from GenBank using the BLAST homology search. Further, a comparison with the known microalgae of the genus *Euglena* on the sequence homology matching degree was made. FIG. 1 shows a comparison table of the base sequence of the 18S rRNA gene of the isolated microalgae of the genus *Euglena* with the base sequence of the 18S rRNA gene of the known microalgae of the genus *Euglena*.

Further, a molecular phylogenetic tree was constructed by the maximum-likelihood method using a molecular phylogenetic tree drawing software Mega5 program (Tamura et al., 2011, Mol. Biol. Evol. 28: 2731-2739). FIG. 2 shows the phylogenetic tree.

As a result, the microalgae isolated as above were identified to be the species belonging to the genus *Euglena* (*Euglena gracilis* Klebs). It should be noted that Ka, Kb, Na, and Nb of the strain EOD-1 in FIG. 2 are symbols denoting test samples of the isolated microalgae. The same result was obtained when using any test sample.

RAPD Analysis

Further, for comparison of the isolated microalgae of the genus *Euglena* with the known microalgae of the genus *Euglena*, the band pattern of the isolated microalgae of the genus *Euglena* and band patterns of 6 strains of the National Institute for Environmental Studies were obtained by RAPD analysis (Random Amplified Polymorphic DNA) (Reference Literature: Williams et al., (1990) Nucleic Aids Res. 18 (22), 6531-6535).

The PCR conditions in the RAPD analysis were as follows.

Sample number: 3

SEQ ID No: 2: AAATCGGGCTG: RAPD-6, Sequence No. 2

Enzyme: Ex Taq (manufactured by Takara Bio Inc.)

Reaction buffer: 50 μL

DNA template amount: about 0.5 ng

PCR temperature conditions: as shown in Table 1; specifically, after a treatment at 94° C. for one minute, a set of treatments (94° C. for one minute, 40° C. for 45 seconds, and 72° C. for one minute) was repeated 35 times, followed by a treatment at 72° C. for 7 minutes.

Electrophoresis conditions: 2.5 mass % agarose gel, 100 V, 40 minutes

TABLE 1

| Cycle operation of PCR | Temperature (° C.) | Time | |
|---|---|---|---|
| Denaturation | 94 | 1 minute | |
| Denaturation | 94 | 1 minute | Repeated 35 times |
| Annealing | 40 | 45 seconds | |
| Elongation | 72 | 1 minute | |
| Elongation | 72 | 7 minute | |

Compared strains in RAPD analysis
Euglena gracilis NIES-47
Euglena gracilis NIES-48
Euglena gracilis NIES-49
Euglena gracilis NIES-253
Euglena gracilis NIES-286
Euglena gracilis NIES-2149

Further, while changing the primer, RAPD analysis was performed in the same manner by the PCR.

SEQ ID No: 3: ATCGGGTCCG: RAPD-4, Sequence No. 3

SEQ ID No: 4: GCGATCCCCA: RAPD-3, Sequence No. 4

The base sequences of the aforementioned primers 2 to 4 are described in Mostafa et al., (2011) Molecules 16, 2598-2608.

Figure 3A:
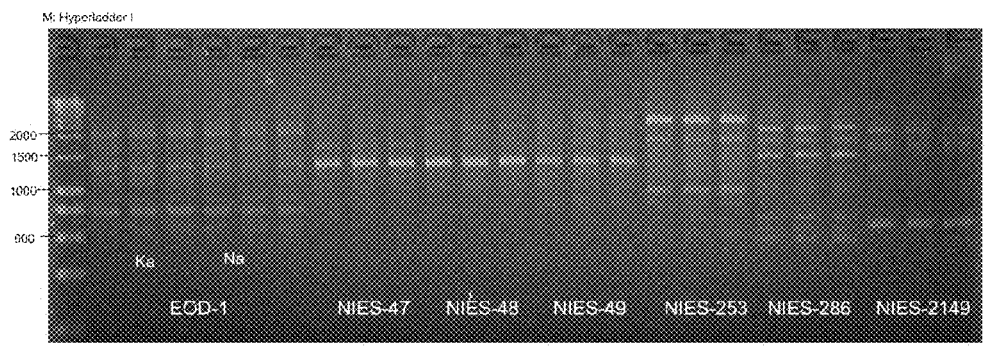
FIG. 3A is an image showing a band pattern in RAPD analysis.
Figure 3B:
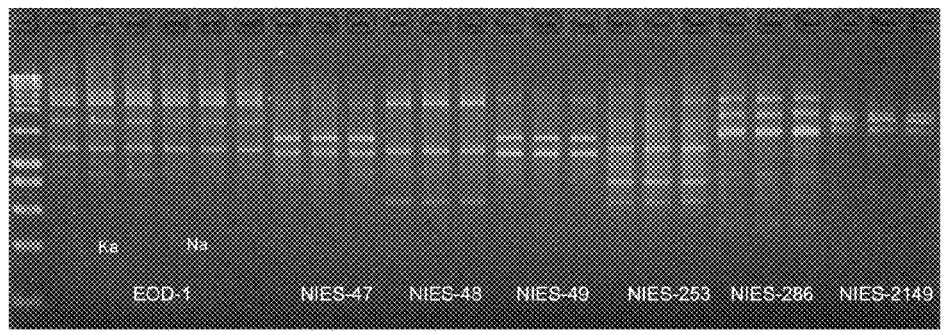
FIG. 3B is an image showing a band pattern in RAPD analysis.
Figure 3C:
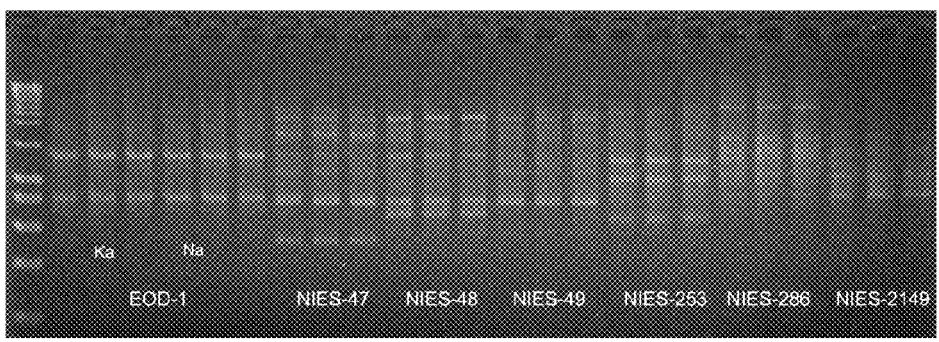
FIG. 3C is an image showing a band pattern in RAPD analysis.

FIG. 3A shows the results (band patterns) of RAPD analysis using the aforementioned primer 1. Further, FIG. 3B and FIG. 3C show the results of RAPD analysis respectively using the aforementioned primers 2 and 3. It should be noted that Ka and Na of strain EOD-1 in FIG. 3A to FIG. 3C respectively correspond to Ka and Na in FIG. 2.

From the results of the RAPD analysis, it has been found that the band patterns of the microalgae of the genus Euglena isolated as above are different from the band patterns of the known microalgae of the genus Euglena. Accordingly, it has been determined that strains of the microalgae of the genus Euglena isolated as above are different from those of the known microalgae of the genus Euglena.

Then, the microalgae of the genus Euglena isolated as above were named Euglena gracilis strain EOD-1.

Culture of Microalgae of the Genus Euglena

In order to culture the microalgae of the genus Euglena, the following materials were prepared and were subjected to a culture step under the following culture conditions.

Microalgae strains of the genus Euglena of the present invention: Microalgae of the genus Euglena (Euglena gracilis) strain EOD-1 (Accession No.: FERM BP-11530) (deposited at the Patent Organism Depositary at the National Institute of Technology and Evaluation)

Known microalgae strains of the genus Euglena: Microalgae of the genus Euglena (Euglena gracilis) strain NIES-48 (obtained from the Microbial Culture Collection at the National Institute for Environmental Studies)

Culture container: as described below, such as a 300-to-500 mL flask

Gas supply to broth: shaking at 130 rpm; air is supplied into the broth by shaking the broth.

Culture temperature: 28° C.

Culture period: as described below pH of broth: as described below

Components in broth for culture: The compositions shown in Table 2 and Table 3 were employed as basic compositions.

The composition shown in Table 2 was obtained by adding components of the composition of "P IV metals" culture medium (disclosed by the Microbial Culture Collection at the National Institute for Environmental Studies) to the composition of "AF-6 culture medium" disclosed by the Microbial Culture Collection at the National Institute for Environmental Studies. Further, the component other than nutrients contained in the broth was water.

Further, the composition shown in Table 3 was based on the composition of Cramer-Myers culture medium.

TABLE 2

| | Composition based on AF-6 Culture Medium |
|---|---|
| $NaNO_3$ | 140 mg/L |
| $NH_4NO_3$ | 22 mg/L |
| $KH_2PO_4$ | 10 mg/L |
| $K_2HPO_4$ | 5 mg/L |
| $MgSO_4 \cdot 7H_2O$ | 30 mg/L |
| $CaCl_2 \cdot 2H_2O$ | 10 mg/L |
| Ferric citrate | 2 mg/L |
| Citric acid | 2 mg/L |
| Biotin | 2 μg/L |
| Thiamine HCl | 10 μg/L |
| $FeCl_3 \cdot 6H_2O$ | 0.98 mg/L |
| $Na_2EDTA \cdot 2H_2O$ | 5 mg/L |
| $MnCl_2 \cdot 4H_2O$ | 0.18 mg/L |
| $CoCl_2 \cdot 6H_2O$ | 0.02 mg/L |
| $ZnSO_4 \cdot 7H_2O$ | 0.11 mg/L |
| $Na_2MoO_4 \cdot 2H_2O$ | 0.0125 mg/L |
| MES | 400 mg/L |
| Vitamin $B_6$ | 1 μg/L |
| Vitamin $B_{12}$ | 1 μg/L |

TABLE 3

| | Composition based on Cramer-Myers Culture Medium |
|---|---|
| $(NH_4)_2SO_4$ | 500 mg/L |
| $KH_2PO_4$ | 500 mg/L |
| $MgSO_4 \cdot 7H_2O$ | 200 mg/L |
| $CaCl_2 \cdot 2H_2O$ | 20 mg/L |
| $Fe_2(SO_4)_3 \cdot 7H_2O$ | 3 mg/L |
| $MnCl_2 \cdot 4H_2O$ | 1.8 mg/L |
| $CoSO_4 \cdot 7H_2O$ | 1.5 mg/L |
| $ZnSO_4 \cdot 7H_2O$ | 0.4 mg/L |
| $Na_2MoO_4 \cdot 2H_2O$ | 0.2 mg/L |
| $CuSO_4 \cdot 5H_2O$ | 0.02 mg/L |
| Vitamin $B_1$ | 0.1 mg/L |
| Vitamin $B_{12}$ | 1 μg/L |

Initial weight of microalgae before culture: 0.78 g/L (dry weight)

Organic nutrients: the following materials were appropriately changed depending on culture.

Glucose

Yeast extract (yeast autolysate): "Dried Yeast Extract D-3" (product name), manufactured by NIHON PHARMACEUTICAL CO., LTD.

Beer as a brewed beverage: Commercially available beer (with a malt use rate of 66.7% or more) containing 5 vol % of ethanol In Examples 1 to 4 and Comparative Examples 1 to 4, heterotrophic culture was performed under dark conditions, and photoheterotrophic culture was performed in the other examples and comparative examples. The culture conditions in the photoheterotrophic culture of microalgae are shown in detail below.

Photoirradiation conditions: after photoirradiation for 12 hours, placed in the dark for 12 hours Light intensity: photosynthetic photon flux density (PPFD) of about 100 μmol/m²·s or about 200 μmol/m²·s

Example 1

200 mL of the composition shown in Table 2 was put into a 500-mL Sakaguchi flask. Further, glucose and yeast extract were added thereto at a glucose concentration of 15 g/L and a yeast extract concentration of 5 g/L. Further, the pH was adjusted to 4.0 by addition of hydrochloric acid. Thus, a broth was prepared.

Then, the flask was shaken under the aforementioned culture conditions and dark conditions (that is, under heterotrophic culture conditions), and microalgae of the genus *Euglena* (*Euglena gracilis*) strain EOD-1 were cultured for 3 days. The culture step was thus performed.

Examples 2 to 4

The culture step was performed in the same manner as in Example 1, except that the amount of glucose was changed so that the glucose concentration in the broth was 20 g/L, 25 g/L, and 30 g/L, respectively.

Comparative Example 1

The culture step was performed in the same manner as in Example 1, except that microalgae of the genus *Euglena* (*Euglena gracilis*) strain NIES-48 were cultured for 5 days instead of the microalgae of the genus *Euglena* (*Euglena gracilis*) strain EOD-1.

Comparative Examples 2 to 4

The culture step was performed in the same manner as in Comparative Example 1, except that the amount of glucose was changed so that the glucose concentration in the broth was 20 g/L, 25 g/L, and 30 g/L, respectively.

The dry weight of the microalgae after the culture step in each of the examples and the comparative examples was measured. Further, the conversion rate of added nutrients was determined by the following calculation formula.

Figure 4:
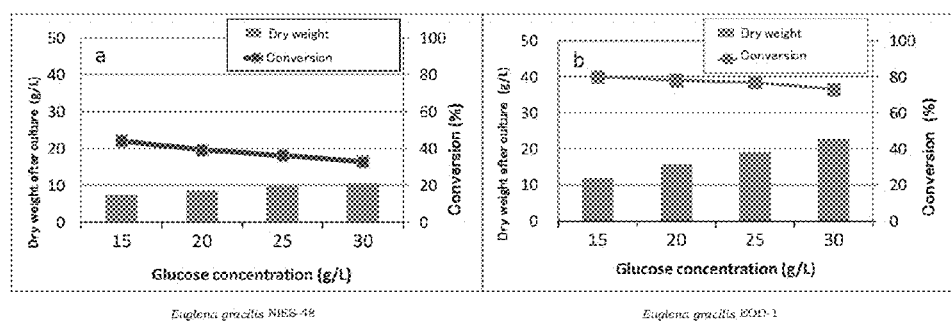
FIG. 4 is a graph showing the glucose conversion of microalgae and the dry weight of microalgae in heterotrophic culture.

Conversion rate (%)=Dry weight (g/L) of algae increased by culture/Concentration (g/L) of consumed glucose FIG. 4 shows the results of the conversion rate and the dry weight of the algae after the culture in each of the examples and the comparative examples As seen from FIG. 4, the microalgae of the genus *Euglena* (*Euglena gracilis*) strain EOD-1 have a higher biomass production than the known strain NIES-48.

Example 5

The culture step was performed by culturing the microalgae of the genus *Euglena* (*Euglena gracilis*) strain EOD-1 in the same manner as in Example 1, except that a 300-ml Erlenmeyer flask was used, a broth obtained by adding beer to 50 mL of the composition shown in Table 2 at a concentration of ethanol derived from beer of 2.5 vol % was used, the yeast extract was not added to the broth, photoirradiation environment for 12 hours and dark environment for 12 hours were repeated during the culture, and the culture period was 7 days. The photosynthetic photon flux density (PPFD) was set to about 100 μmol/m$^2$·s.

Example 6

The culture step was performed in the same manner as in Example 5, except that the yeast extract was added to the broth at a concentration of the yeast extract of 2 g/L.

Comparative Example 5

The culture step was performed in the same manner as in Example 5, except that microalgae of the genus *Euglena* strain NIES-48 were cultured instead of the microalgae of the genus *Euglena* (*Euglena gracilis*) strain EOD-1.

Comparative Example 6

The culture step was performed in the same manner as in Comparative Example 5, except that the yeast extract was added to the broth at a concentration of the yeast extract of 2 g/L.

Figure 5:
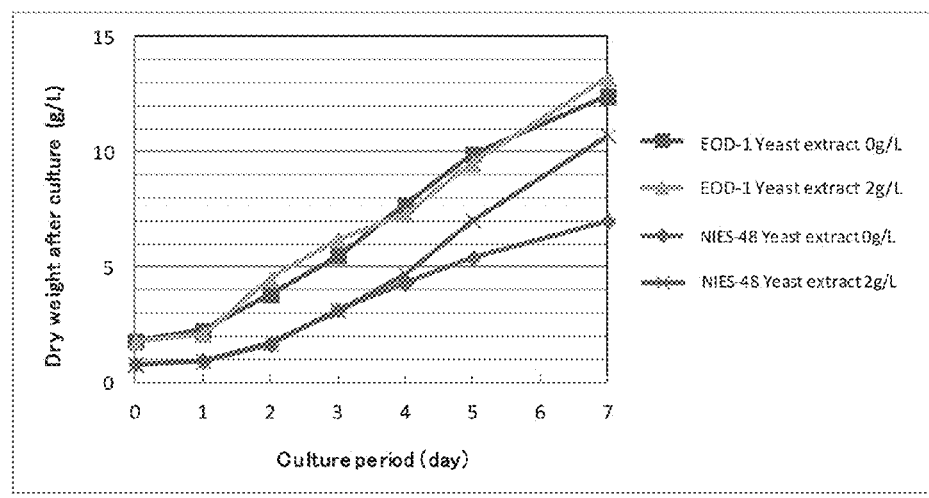
FIG. 5 is a graph showing the culture period of microalgae and the dry weight of microalgae in photoheterotrophic culture.

In the culture step of each of Examples 5 and 6, and Comparative Examples 5 and 6, the dry weight of microalgae after the culture for 1, 2, 3, 4, 5, and 7 days was measured. FIG. 5 shows the results.

As seen from FIG. 5, the microalgae of the genus *Euglena* (*Euglena gracilis*) strain EOD-1 have higher productivity than the known strain NIES-48, even when they were cultured under photoheterotrophic culture conditions.

Examples 7 to 12

The culture step was performed in the same manner as in Example 5, except that the composition shown in Table 3 was used instead of the composition shown in Table 2, the initial pH of the broth was changed to pH 5.5, pH 6.0, pH 7.0, pH 8.0, pH 8.5, and pH 9.0, respectively, and the culture period was changed to 10 days.

Figure 6:
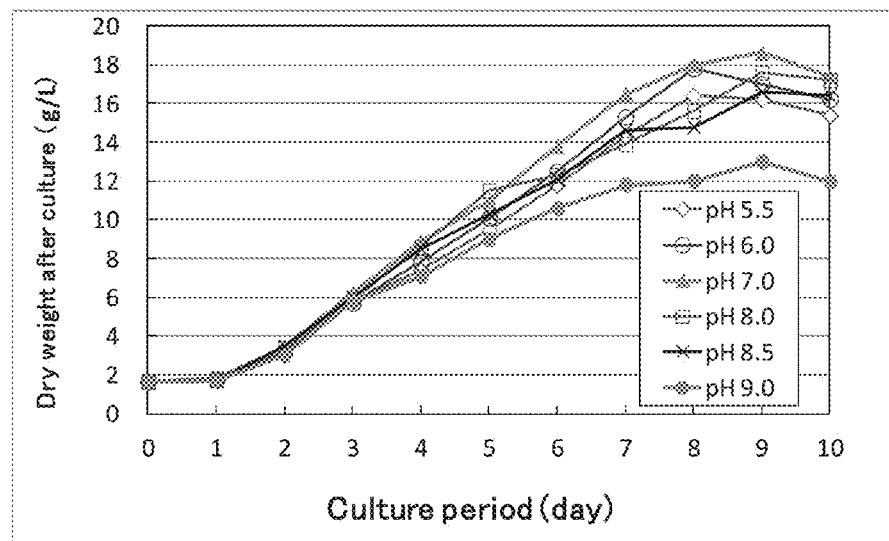
FIG. 6 is a graph showing the culture period of microalgae and the dry weight of microalgae in photoheterotrophic culture using culture media under different pH conditions.

In the culture step of each of Examples 7 to 12, the dry weight of the microalgae after the culture was measured over time. FIG. 6 shows the results.

Examples 13 to 17

The culture step was performed in the same manner as in Example 5, except that the composition shown in Table 3 was used instead of the composition shown in Table 2, the photosynthetic photon flux density (PPFD) was set to about 200 μmol/m$^2$·s, the initial pH of the broth was changed to pH 3.5, pH 4.0, pH 4.5, pH 5.0, and pH 5.5, respectively, and the culture period was changed to 10 days.

Examples 18 and 19

The culture step was performed in the same manner as in Example 5, except that the composition shown in Table 3 was used instead of the composition shown in Table 2, the initial pH of the broth was changed to pH 3.5 and pH 5.5, respectively, and the culture period was changed to 10 days.

Figure 7:
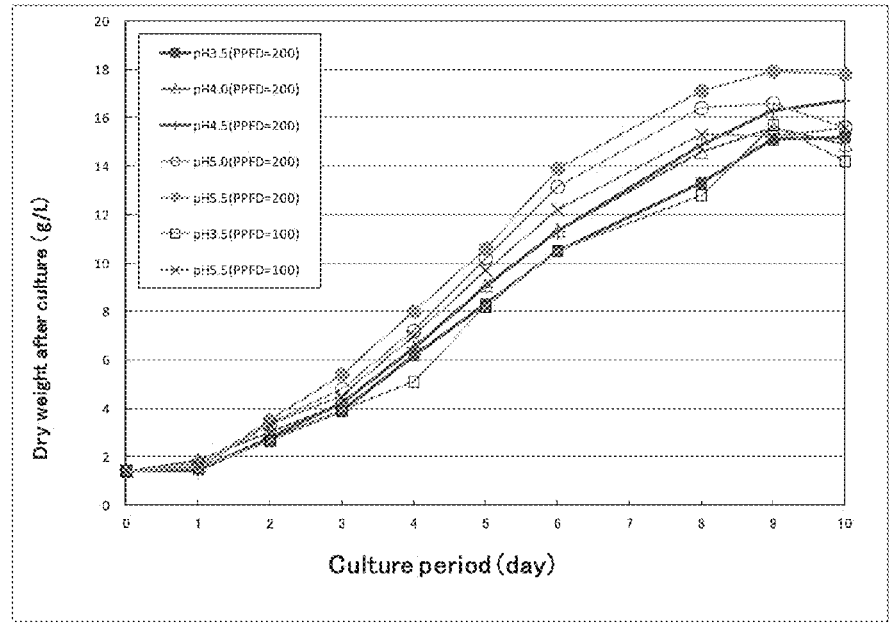
FIG. 7 is a graph showing the culture period of microalgae and the dry weight of microalgae in photoheterotrophic culture using culture media under different pH conditions.

In the culture step of each of Examples 13 to 19, the dry weight of the microalgae after the culture was measured over time. FIG. 7 shows the results.

Example 20

The culture step was performed by culturing the microalgae of the genus *Euglena* (*Euglena gracilis*) strain EOD-1 in the same manner as in Example 5, except that the culture period was 7 days.

The culture was performed under aerobic conditions by shaking the flask until two days after the culture start. Thereafter, the shaking was stopped, and the culture was performed under anaerobic conditions by supplying an inert gas (nitrogen gas).

Comparative Example 7

The culture step was performed in the same manner as in Example 20, except that microalgae of the genus *Euglena* (*Euglena gracilis*) strain NIES-48 were cultured instead of the microalgae of the genus *Euglena* (*Euglena gracilis*) strain EOD-1.

The culture was performed under aerobic conditions by shaking the flask until 4 days after the culture start. Thereafter, the shaking was stopped, and the culture was performed under anaerobic conditions by supplying an inert gas (nitrogen gas).

The amounts of paramylum and lipids (wax esters) produced by the culture in Example 20 and Comparative Example 7 were measured every day.

The paramylum amount after the culture was measured by the following procedure. That is, a mixture (40 mL) of the broth and the microalgae after the culture was put into a centrifugal tube, followed by centrifugation. Pure water was added to the precipitate after the centrifugation to yield a suspension, and the operation of centrifugal re-separation was repeated twice. Then, a small amount of pure water was added to the precipitate after the centrifugation to yield a suspension, and the suspended solids were freeze-dried. Thus, the components of the broth were removed.

Next, about 400 mg of the cells of the freeze-dried microalgae was accurately weighed out in a centrifugal tube (which had been weighed as a blank value). Acetone was added thereto to yield a suspension, and the supernatant fluid after centrifugation was removed. Until the color of the supernatant fluid disappears, the washing operation with acetone was repeated about 5 times. Thus, the pigment components produced by the microalgae were removed.

Subsequently, using a dodecyl sodium sulfate solution, an operation to remove components other than paramylum was performed. That is, 20 mL of a 1% dodecyl sodium sulfate (SDS) solution was added to the residue after the pigment components were removed so as to yield a suspension, which was thereafter heated at 100° C. for 10 minutes. Then, the supernatant fluid after centrifugation was removed. Such an operation was repeated twice, and thereafter the same operation was repeated three times using pure water instead of the SDS solution. Thus, the SDS was washed away.

Finally, the whole centrifugal tube was put in a dryer at 105° C. so that the moisture was removed, and the weight of the centrifugal tube containing paramylum was measured. Then, the amount of paramylum was determined from the difference from the aforementioned blank value.

Meanwhile, the amount of wax esters after the culture was measured by the BLIGHT-DYER method.

Figure 8A:
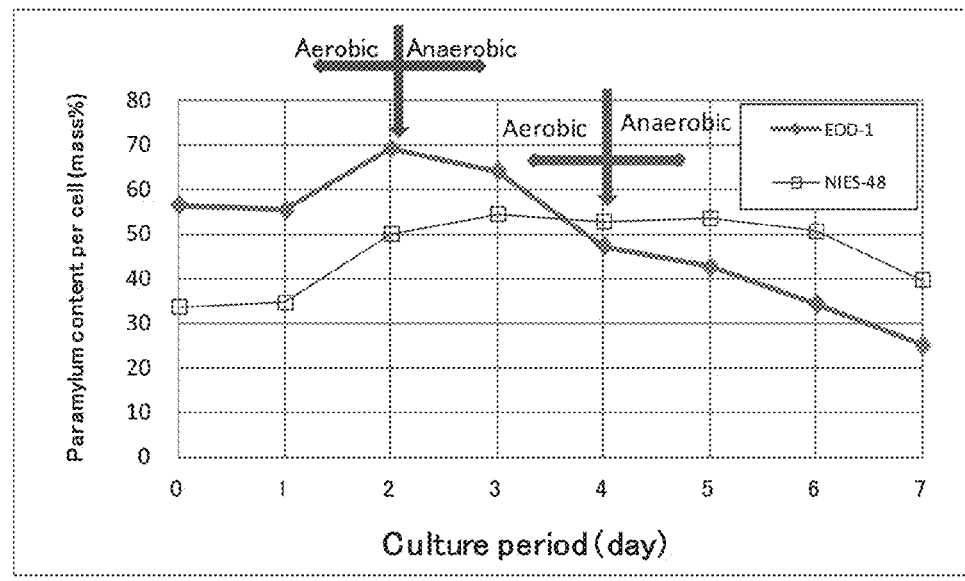
FIG. 8A is a graph showing the culture period of microalgae and the paramylum content per cell when the conditions change from aerobic to anaerobic in photoheterotrophic culture.
Figure 8B:
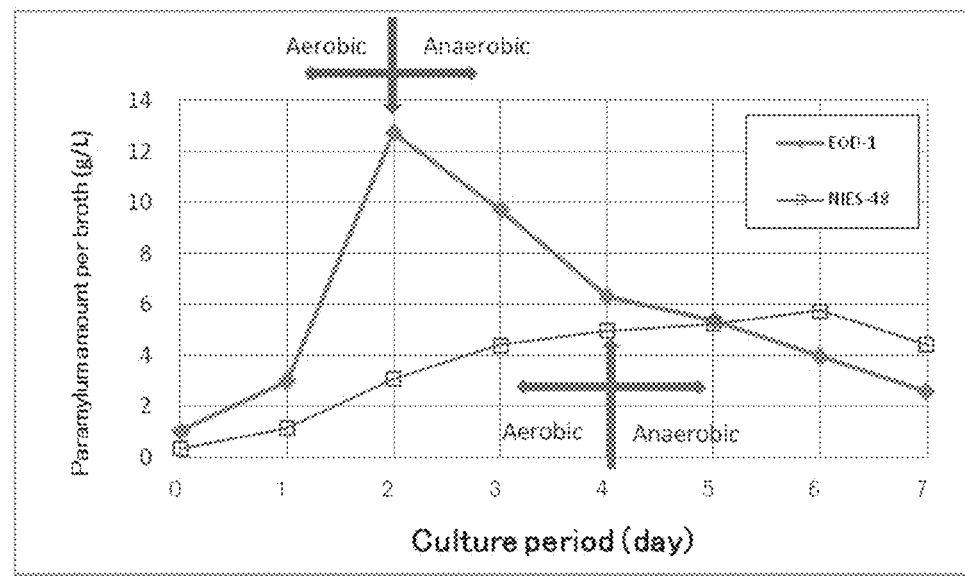
FIG. 8B is a graph showing the culture period of microalgae and the paramylum amount per broth when the conditions change from aerobic to anaerobic in photoheterotrophic culture.

FIG. 8A and FIG. 8B show the measurement results of the paramylum amount over time in the culture of Example 20 and Comparative Example 7. Further, FIG. 9A and FIG. 9B show the measurement results of the lipid (wax ester) amount over time.

As seen from FIG. 8A and FIG. 8B, the microalgae of the genus *Euglena* (*Euglena gracilis*) strain EOD-1 have a higher paramylum production speed than the conventional microalgae of the genus *Euglena* (*Euglena gracilis*) strain NIES-48. Further, the strain EOD-1 has a paramylum content per cell of about 55% or more, which is higher than in the strain NIES-48.

Figure 9A:
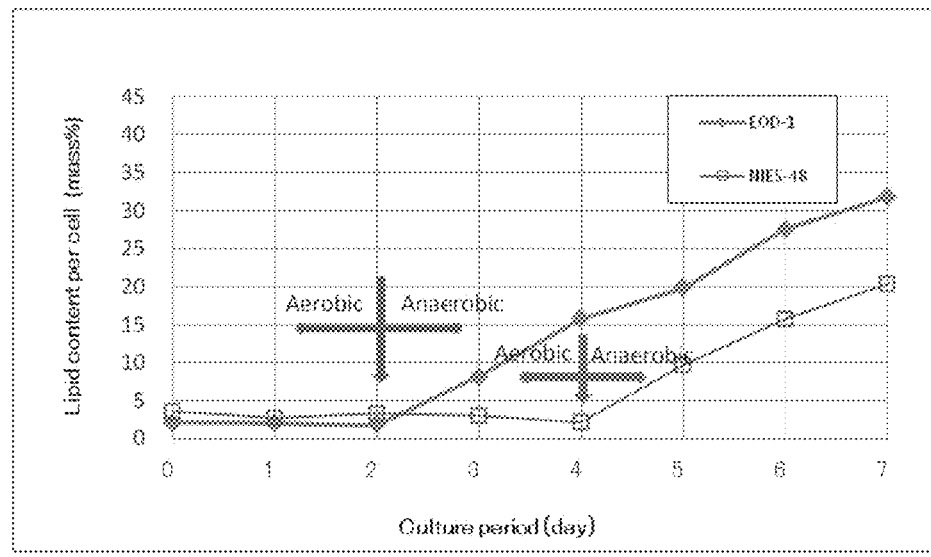
FIG. 9A is a graph showing the culture period of microalgae and the lipid content per cell when the conditions change from aerobic to anaerobic in photoheterotrophic culture.
Figure 9B:
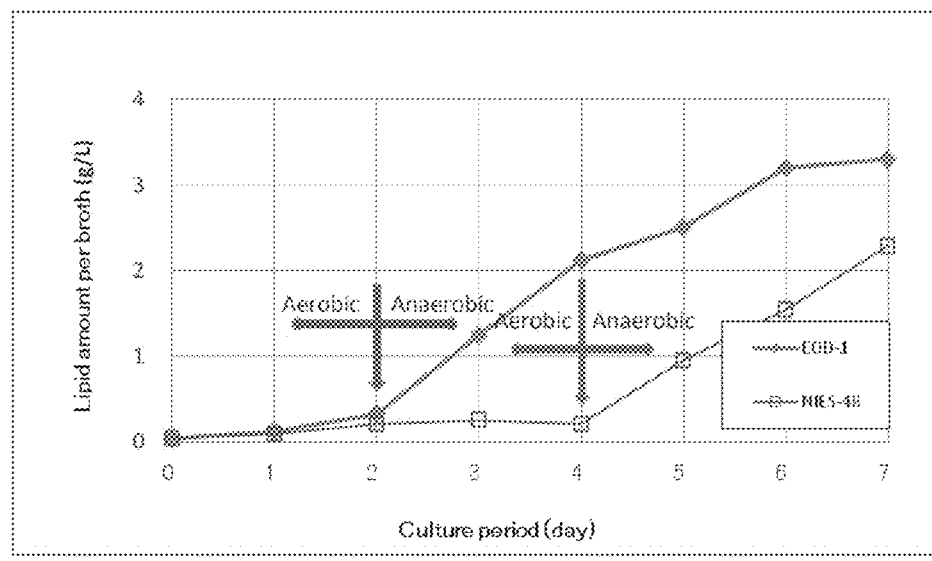
FIG. 9B is a graph showing the culture period of microalgae and the lipid amount per broth when the conditions change from aerobic to anaerobic in photoheterotrophic culture.

Further, as seen from FIG. 9A and FIG. 9B, the microalgae of the genus *Euglena* (*Euglena gracilis*) strain EOD-1 have a higher lipid (wax ester) production speed, and thus the content of wax esters per cell is increased within a shorter period.

Further, the culture step was performed using the culture medium having the composition shown in Table 4 and Table 5 below under the following culture conditions.

Example 21

The aforementioned microalgae, strain EOD-1, were cultured for two days by photoheterotrophic culture.

Comparative Example 8

The aforementioned microalgae, strain NIES-48, were cultured for two days by photoheterotrophic culture.

As the culture medium, a culture medium obtained by adding 30 g/L of glucose to a modified Hutner culture medium (hereinafter, referred to as "Modified Hutner culture medium") was employed. Specifically, the composition was as shown in Table 4, and the component in the liquid other than nutrients was water. As the trace metal solution in Table 4, a trace metal solution having the composition in Table 5 below was used. The component other than trace metal was water.

The detailed culture method was as follows.

Broth: with a pH adjusted to 4.0 using hydrochloric acid

Culture container: 500-mL Sakaguchi flask

Introduction before the culture: 200 mL of the broth and the microalgae before the culture were put into the Sakaguchi flask (in order to adjust the initial amount of biomass, 220 mL in total was used for the strain EOD-1 and 236 mL in total was used for the strain NIES-48).

Temperature during culture: 28° C.

Light-dark conditions during culture: cultured under light-shielded dark conditions Aerobic conditions during culture: The Sakaguchi flask was placed on a shaker, and air was supplied into the broth by operating the shaker with reciprocal shaking at 130 rpm.

TABLE 4

| Modified Hutner Culture Medium: Glucose Added | |
|---|---|
| Glucose | 30 g/L |
| Asparagine | 2 g/L |
| Glutamic acid | 5 g/L |
| Malic acid | 5 g/L |
| Glycine | 2.5 g/L |
| Urea | 0.4 g/L |
| Succinic acid | 0.1 g/L |
| $KH_2PO_4$ | 0.4 g/L |
| $MgSO_4 \cdot 7H_2O$ | 0.14 g/L |
| $MgCO_3$ | 0.4 g/L |
| $CaCO_3$ | 0.1 g/L |
| $(NH_4)_2Fe(SO_4)_2 \cdot 6H_2O$ | 0.021 g/L |
| Vitamin $B_1$ | 0.6 mg/L |
| Vitamin $B_{12}$ | 0.05 mg/L |
| Trace metal solution | 10 mL/L |

TABLE 5

| | |
|---|---|
| $ZnSO_4 \cdot 7H_2O$ | 1.1 g/L |
| $MgSO_4 \cdot H_2O$ | 0.58 g/L |

TABLE 5-continued

| | |
|---|---|
| $(NH_4)_6Mo_7O_{24} \cdot 4H_2O$ | 0.18 g/L |
| $CoSO_4 \cdot 7H_2O$ | 0.024 g/L |
| $CuSO_4 \cdot 5H_2O$ | 0.077 g/L |
| $H_3BO_3$ | 0.029 g/L |
| $NaNO_3 \cdot 4H_2O$ | 0.074 g/L |

The dry weight (biomass production) of the algae after two days from the culture and the glucose conversion were calculated in the same manner as above. Table 6 shows the results.

TABLE 6

| After two days from the culture | Ex. 21 (Strain EOD-1) | C. Ex. 8 (Strain NIES-48) |
|---|---|---|
| Dry weight (g/L) | 24.50 | 11.50 |
| Glucose conversion (%) | 76 | 33 |

As seen from Table 6, the microalgae of the genus Euglena (*Euglena gracilis*) strain EOD-1 have a better biomass production performance and a better glucose conversion than the conventional microalgae of the genus Euglena (*Euglena gracilis*) strain NIES-48.

The microalgae of the present invention, the method for producing polysaccharides of the present invention, and the method for producing an organic compound of the present invention are suitably used for obtaining organic compounds such as polysaccharides such as paramylum, lipids such as wax esters, and proteins by culture.

The obtained organic compounds can be used in applications such as health food, pharmaceutical, feed, chemical products, or fuel, while remaining stored in the cells of the microalgae, or after being extracted by an extraction process or the like. Specifically, the lipids stored in the cells of the microalgae as organic compounds by culture are suitably used, for example, as a raw material of fuel by being extracted from the cells.

The invention claimed is:

1. A method for producing polysaccharides comprising:
    culturing, on a culture medium, a microalgae of the genus *Euglena* that is *Euglena gracilis* strain EOD-1 deposited under Accession No. FERM BP-11530 to produce the polysaccharides.

2. The method for producing polysaccharides according to claim 1, wherein a broth used in the culture medium contains 15 to 30 g/L of glucose.

3. The method for producing polysaccharides according to claim 2, wherein the broth used in the culture medium contains yeast lysate.

4. The method for producing polysaccharides according to claim 1, wherein the polysaccharides are paramylon.

5. A method for producing an organic compound comprising:
    culturing *Euglena gracilis* strain EOD-1 deposited under Accession No. FERM BP-11530 to produce at least one organic compound selected from the group consisting of polysaccharides, lipids, vitamin C, vitamin E, pigments, and proteins.

6. A method for producing food comprising a microalgae of the genus *Euglena*, the method comprising:
    drying a microalgae of the genus *Euglena*, wherein the microalgae is *Euglena gracilis* strain EOD-1 deposited under Accession No. FERM BP-11530, and wherein the microalgae has been cultured according to the method of claim 1; and
    incorporating the dried microalgae into a food.

* * * * *